United States Patent [19]

Tomlinson

[11] Patent Number: 4,592,842
[45] Date of Patent: Jun. 3, 1986

[54] METHOD AND APPARATUS FOR OPTIMIZING PEAK DETECTION IN A CHROMATOGRAM

[75] Inventor: Barrett L. Tomlinson, Santa Clara, Calif.

[73] Assignee: Spectra-Physics, Inc., San Jose, Calif.

[21] Appl. No.: 587,577

[22] Filed: Mar. 8, 1984

[51] Int. Cl.⁴ .............................................. B01D 15/08
[52] U.S. Cl. .................................. 210/659; 210/198.2; 422/70
[58] Field of Search ............ 210/635, 656, 659, 198.2; 55/67, 386; 422/70

[56] References Cited

U.S. PATENT DOCUMENTS

| | | | |
|---|---|---|---|
| 3,508,880 | 4/1970 | Hrdina | 210/659 |
| 4,290,776 | 9/1981 | Yamada | 210/659 |
| 4,364,263 | 12/1982 | Sankoorikal et al. | 210/198.2 |
| 4,455,084 | 6/1984 | Webb, Jr. et al. | 210/659 |
| 4,468,331 | 8/1984 | Antle et al. | 210/659 |
| 4,478,721 | 10/1984 | Gerhold | 210/659 |

Primary Examiner—John Adee
Attorney, Agent, or Firm—Donald C. Feix

[57] ABSTRACT

Methods of and apparatus for identifying peaks corresponding to the same chemical component in a series of liquid chromatograms to identify the peaks without foreknowledge of the chromatographic behavior of any component in the sample, or even the number of components in the sample.

9 Claims, 10 Drawing Figures

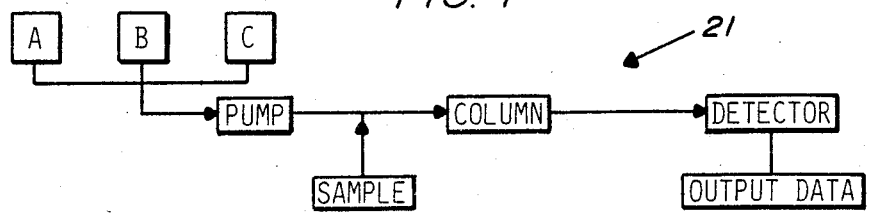
FIG. 1
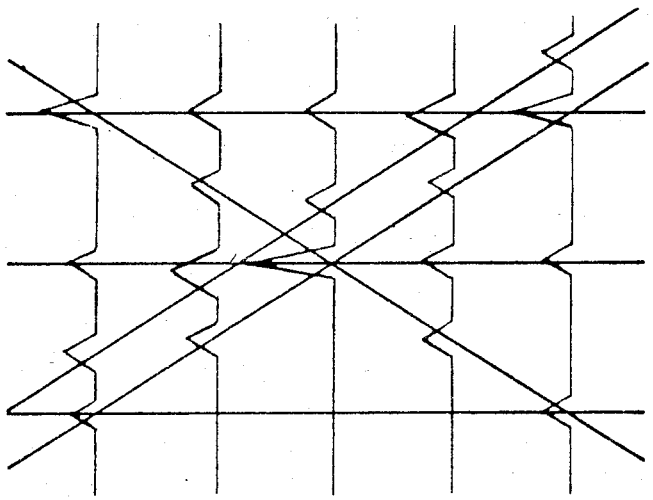
FIG. 4
EACH COMPONENT IS RESOLVED
IN AT LEAST ONE CHROMATOGRAM
FIG. 5
CHROMATOGRAPH THE SAMPLE
FIVE TIMES USING THE ELUENT
COMPOSITIONS:
1. AB
2. .75 AB + .25 AC
3. .5  AB + .5  AC
4. .25 AB + .75 AC
5. AC

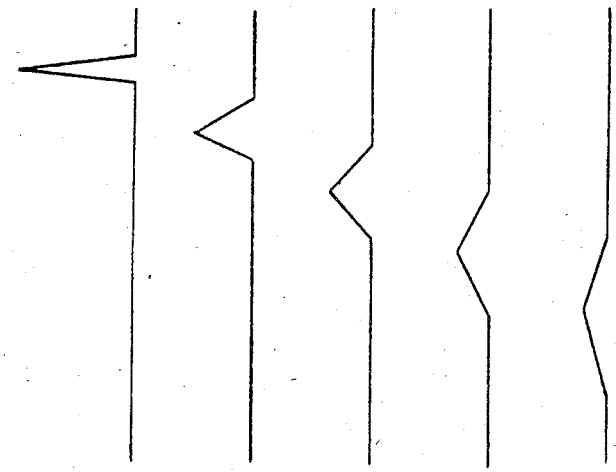
PEAK AREA IS PROPORTIONAL
TO COMPONENT CONCENTRATION
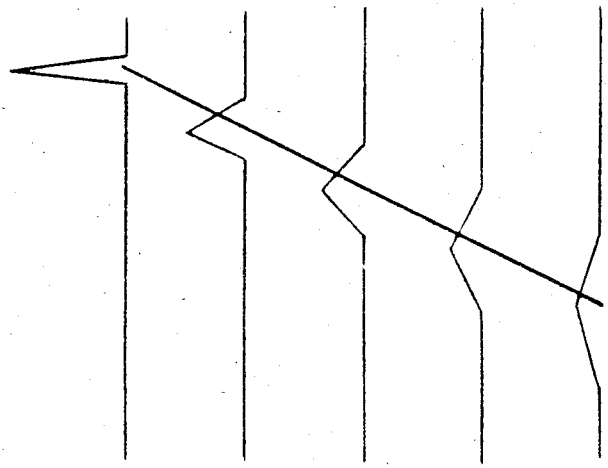
RETENTION TIME IS A LINEAR
FUNCTION OF ELUENT COMPOSITION

NORMALIZE ALL CHROMATOGRAMS
TO AREA %

NORMALIZE RETENTION TIMES:

$\Sigma$ Area$_i$ Retention Time$_i$
IS CONSTANT FOR ALL CHROMATOGRAMS

FIG. 8

FIND BEST LINEAR FIT WITH LEAST ERROR

FIG. 9

SAMPLE CONTAINING METHYL, ETHYL, PROPYL PARABENS & ANISOLE

CHROMATOGRAPHED AT 1 ML/MIN ON 10 CM RP8 SPHERI-5 MPLC CARTRIDGE AT AMBIENT TEMPERATURE

IN FOLLOWING ELUENTS

| # | WATER | METHANOL | THF |
|---|---|---|---|
| 1 | 50% | 50% | |
| 2 | 55% | 37% | 8% |
| 3 | 60% | 25% | 15% |
| 4 | 65% | 13% | 22% |
| 5 | 71% | | 29% |

METHOD AND APPARATUS FOR OPTIMIZING PEAK DETECTION IN A CHROMATOGRAM

BACKGROUND OF THE INVENTION

This invention relates to methods of and apparatus for identifying peaks corresponding to the same chemical component in a series of liquid chromatograms.

The present invention relates particularly to methods and apparatus for identifying the peak in each chromatogram corresponding to the same component without foreknowledge of the chromatographic behavior of any component in the sample, or even the number of components in the sample.

Optimizing the separation of chemical components in a sample has presented problems with prior art liquid chromatographic techniques. The problem can be particularly difficult when two or more chemical components would normally try to elute fairly close together on a specific column and with a specific eluent.

The prior art liquid chromatographic techniques have included chromatographing a sample using several different eluents composed of varying mixtures of two binary eluents to try to find an eluent composition which maximizes the minimum difference of any pair of peaks in the chromatogram.

For many samples the prior art techniques have required isolation of each of the components of the sample and have required so many experiments to resolve the informaton required that the prior art techniques have been essentially impractical.

The prior art techniques have required, for many samples, that the separation be developed by someone who is skilled in the art of chromatography and who could understand the chromatograhic behavior experimentally of each of the components of the sample.

It is a primary object of the present invention to avoid the problems presented by the prior art techniques and to maximize the minimum difference of any pair of peaks in a chromatogram by methods and apparatus which do not require involvement of someone skilled in the art of chromatography.

It is a closely related object of the present invention to separate the minimum difference in retention times of different components as much as possible and to do so by methods and apparatus which do not require foreknowledge of the chromatographic behavior of any component in the sample or even the number of components in the sample.

Other objects of the present invention include developing a technique to identify the number of components in a sample, correlating the components retention time as a function of eluent composition, determining the optimal separation based on a minimal number of chromatographic separations of a sample of unknown composition and developing a technique which correctly handles a chromatographic system having multiple peak reversals or peak fusions.

SUMMARY OF THE INVENTION

The methods and apparatus of the present invention identify peaks corresponding to the same chemical component in a series of liquid chromatograms.

The methods and apparatus comprise chromatographing a sample using several different eluents of approximatly the same eluent strength, said eluents being composed of varying mixtures of two binary eluents.

The methods and apparatus of the present invention create a model and evaluate the correspondence of the model to the data.

The retention times and areas of all peaks in each chromatogram are determined.

Combinations of peaks are formed, one peak from each chromatogram, such that the set of all combinations of peaks formed is guaranteed to contain a combination of peaks all corresponding to one chemical component of the chromatogram.

Each combination of peaks in said set is tested by determining the equation of the straight line best describing peak retention times as a function of eluent compositions and by computing the relative standard deviations of the set of straight lines to the retention times of the peaks of said combination.

The present invention selects the peak combination and associated straight line factor having the lowest relative standard deviation of any peak combination of the set as contained peaks all corresponding to the same chemical component.

The minimum peak area in the identified peak combinations is determined.

The present invention removes said minimum peak area from peaks having the retention times of the identified peak configuration; thereby removing this peak area from the collection of peak retention times in areas not identified in each chromatogram.

The formation of sets of peak combinations, testing, selecting, determining and removing are repeated until all areas in one chromatogram are assigned or until the relative standard deviation of the best fit straight line exceeds some pre-set threshold.

The present invention thus restricts the number of peaks that are examined, and this is a key to the success of the present invention.

The strategy used in the present invention insures that the set of all combinations of peaks formed is guaranteed to contain a combination of peaks all corresponding to one chemical component of the chromatogram.

The present invention generates an extraneous indication which results from system errors if the relative standard deviation of the best fit straight line exceeds some pre-set threshold.

In preferred embodiments of the present invention all the peak areas of each chromatogram are normalized such that the sum of the areas of all the peaks in each chromatogram is constant and all retention times of all peaks in each chromatograms are normalized such that the sum overall peaks of each chromatogram of the product of normalized peak area and peak retention times is constant.

In a specific embodiment of the present invention the method and apparatus described above is applied to a ternary system.

The present invention is, however, also applicable to quaternary systems, and in such systems the present invention fits a plane, rather than a straight line only, to the data points.

The method and apparatus of the present invention is also readily generalized to other multi-solvent systems.

The present invention focuses on the conservation of area function of the chromatograms and uses this to constrain the problem. The present invention allows the handling of overlapping peaks and restricts the number of trial fits.

The present invention works from the largest area to the smallest to get one true fit and does not consider all possible fits.

The present invention fits the retention times to a function to predict the retention times; it uses a correlation of peak retention times as a primary determinant of peaks corresponding to the same component.

Methods and apparatus for identifying the peak in each chromatogram corresponding to the same component and having the features described above and effective to function as described above constitute specific objects of the present invention.

Other and further objects of the present invention will be apparent from the following description and claims and are illustrated in the accompanying drawings which, by way of illustration, show preferred embodiments of the present invention and the principles thereof and what are now considered to be the best modes contemplated for applying these principles. Other embodiments of the invention embodying the same or equivalent principles may be used and structural changes may be made as desired by those skilled in the art without departing from the present invention and the purview of the appended claims.

BRIEF DESCRIPTION OF THE DRAWING VIEWS

FIG. 1 is a diagramatic view showing a ternary solvent eluent liquid chromatographic system in which the methods and apparatus of the present invention can be embodied.

FIGS. 2, 3 and 4 are views illustrating assumptions on which the method and apparatus of the present invention are based.

FIGS. 5, 6, 7 and 8 are views illustrating steps used in one specific embodiment of the method and apparatus of the present invention.

FIGS. 9 and 10 are views illustrating one example of a sample having four components chromatographed in accordance with the present invention.

FIG. 9 lists the components of the sample and the binary mixtures of the eluents.

Figure 10:
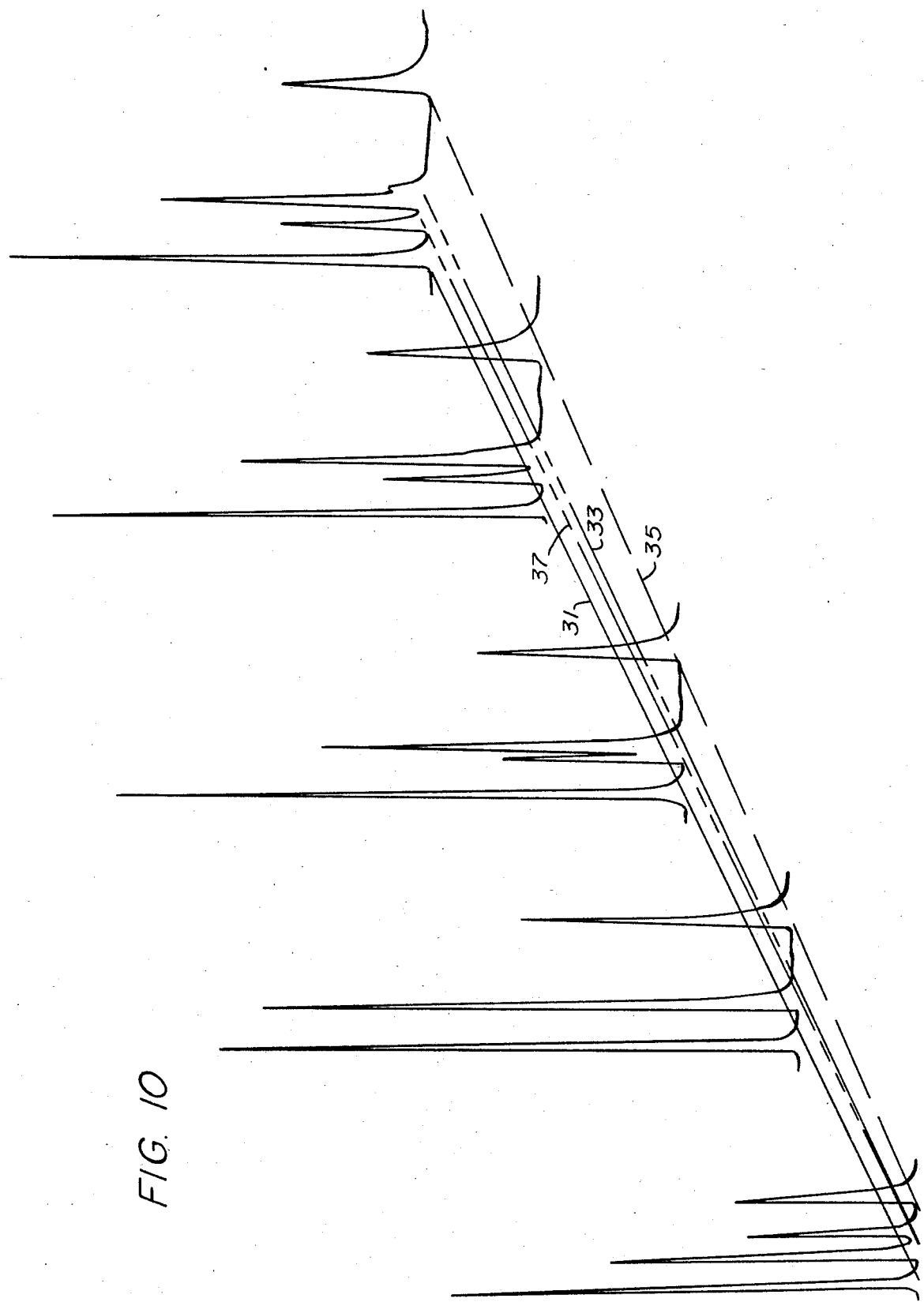

FIG. 10 shows how the series of liquid chromatographs is used to identify peaks corresponding to the same chemical component in accordance with the present invention.

DESCRIPTION OF THE PREFERRED EMBODIMENTS

A liquid chromatograph system of the kind with which the methods and apparatus of the present invention can be utilized is indicated generally by the reference numeral 21 in FIG. 1.

The system 21 is a ternary solvent eluent system, and the description of a preferred embodiment of the present invention to follow will be made in reference to such a ternary solvent eluent system. It should be noted, however, that the methods and apparatus of the present invention are applicable to quaternary and other multi-solvent systems.

The system 21 chromatographs a sample using an eluent composed of a mixture of two binary eluents (e.g., water plus an organic modifier). These eluents are indicated by letters A, B and C in FIG. 1. The system 21 includes a pump, a column, means for injecting a sample into the line flowing from the pump to the column, a detector, and means for obtaining output data, which is generally an integrating computer, all as indicated in FIG. 1.

The starting point in the present invention, with the ternary system shown in FIG. 1, is an appropriate mixture of A–C and an appropriate mixture of A–B. The present invention will then determine the appropriate mixture of A–B and A–C.

There are a number of ways to find an appropriate mixtures of A–B and an appropriate mixture of A–C.

The appropriate mixture A–B may, for example, be determined by automated chromatographic mechanisms which are commercially available.

When the strength of A–B is known, there are formulas in literature which determine approximately what the composition of A–C should be. The A–C combination can also be determined experimentally.

The present invention utilizes the appropriate A–B mixture and appropriate A–C mixture to look at linear combinations of those two mixtures for determining the best eluent composition for maximizing the minimum difference of any pair of peaks in the chromatograms.

The present invention recognizes that peak retention volume is a function of eluent composition (strength and eluent selectivity).

The present invention uses techniques responsive to this function; it applies linearization techniques to peak retention data to make the function linear (to the extent that it is not already linear) and permits determining the best eluent composition.

With the ternary system shown in FIG. 1, the sample is chromatographed in five mixtures of these binary eluents. The peak retention times and areas of each of these chromatograms are determined. A technique which is described in more detail below is used to identify peaks corresponding to the same component in each chromatogram. Functions describing the retention time of each component as a function of eluent composition are developed. Finally, the functions modeling the retention times of all the components are solved to find the eluent composition at which all samples are best resolved.

The core of this technique is a method of identifying the peaks in each chromatogram corresponding to the same component without foreknowledge of the chromatographic behavior of any component in the sample, or even the number of components in the sample.

This technique rests on four assumptions about the chromatographic systems. These assumptions are:

1. The peak area is proportional to component concentration and independent of peak shape. The technique proposed depends on this. Thus, one could not use peak height as peak height is dependent on peak width, which typically varies with retention time in an isocratic system. Likewise, one could not use flow programming with this technique, as peak area would depend on flow rate at the time of elution. FIG. 2 illustrates this assumption 1.

2. Retention time is a linear function of eluent composition. This is not always strictly true, but the invention shows a way of compensating for first order deviations from this assumption. With this compensation, the assumption has proven to be remarkably accurate for the systems that have been examined, when chromatographed using the reverse phase separation mechanism. FIG. 3 illustrates this assumption number 2.

3. Each component is resolved in at least one chromatogram. FIG. 4 illustrates this assumption. FIG. 4 shows in an intentionally complex case that this is a remarkable lenient requirement. This case shows that the assumption can be met even in those cases in which all components are resolved.

It is crucial to note here, however, that the technique is limited to identifying and tracking only components which are resolved in at least one chromatogram. The technique will not detect the presence of two components which elute as a single peak under all chromatographic conditions examined.

4. The fourth and last assumption is that all components are present, detected and integrated under all chromatographic conditions used. This means that no peaks are lost off the end of the chromatogram, and that no peaks miss being integrated by the computing integrator.

The system will now be examined in operation.

The first step is to select two binary eluent compositions of the desired eluent strength.

The sample is chromatographed using the two binary eluents and three intermediate ternary mixtures. See FIG. 5.

Figure 6:
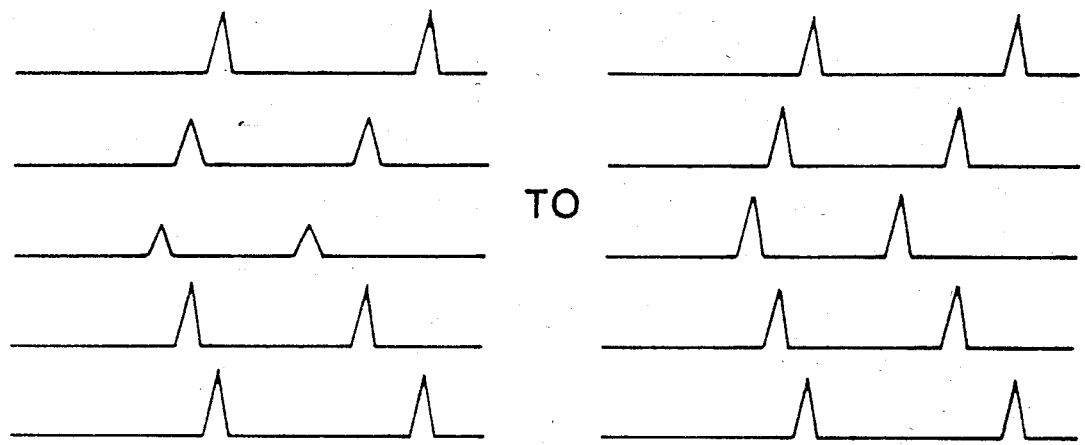

The area of the peaks in all chromatograms are preferably normalized so that each chromatogram has the same total peak area. This is equivalent to an area percent normalization. Normalization compensates for any small variation in sample concentration or injection volume. See FIG. 6 which illustrates this normalization.

Figure 7:
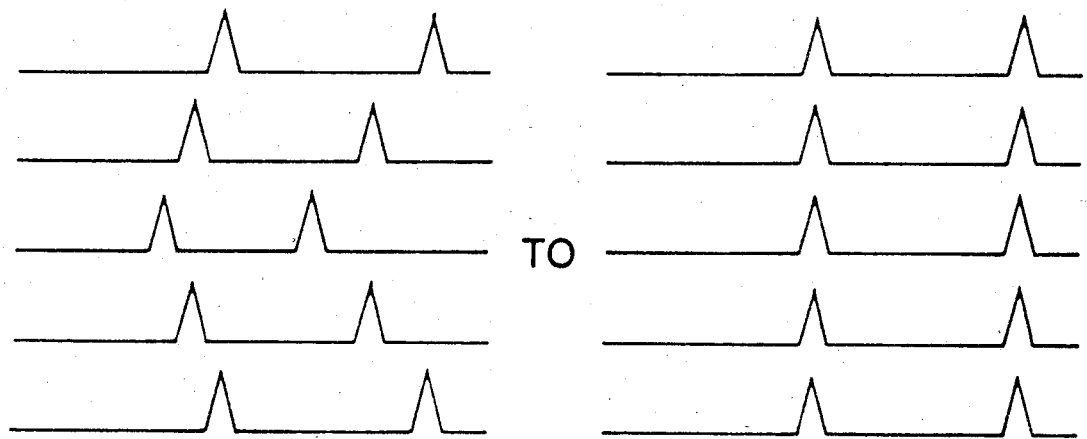

Next, the retention times are preferably normalized so that each chromatogram has the same weighted average retention time. The retention times are weighted by the area of the peak. This step has the virtue of compensating to first order for situations where the elution strength of a ternary mixture is not the same as the interpolated strength of its binary components. See FIG. 7 showing this normalization.

Using these normalized peak areas and retention times, peaks are identified corresponding to the same component. See FIG. 8.

It is sought to describe the retention time behavior of peak area as a linear function eluent composition. To do this one peak is selected from each chromatogram. A straight line is computed best describing the retention times of these peaks as a function of eluent composition. The relative standard deviation of the fit of the peak retention times to the straight line is then computed. This procedure is repeated for all possible combinations of peaks which might correspond to the same component.

Under the assumption (noted above) the set of peaks corresponding to the same component is that combination of peaks giving the lowest relative standard deviation to their best fit straight line.

For example, FIG. 8 shows two possible combinations of peaks corresponding to the same component. The best fit straight line is shown for each combination. Obviously, the peak combination on the left is a better fit to the straight line and would be the set identified.

Once a combination of peaks is identified as corresponding to a single component, the peak areas are examined. Under the assumption, at least one area corresponds to the pure component. If there are significant variations among the areas of the peaks, the smallest area is selected. The identified set of peak areas is then removed from the collection of peaks to be fit.

This process is repeated until it is not possible to find a reasonable fit to a straight line among the remaining peak combinations, or until all peak areas are assigned in at least chromatogram.

The straight line functions describing the retention time behavior may then be solved to find the eluent composition in which the components identified are best resolved.

If all peak combinations are tried in search of a component identification, the number of calculations will rise proportional to at least the fourth power of the number of peaks in the chromatogram. This obviously would limit the complexity of the sample which could be handled by this method. Fortunately, it is possible by straightforward techniques to limit the number of peak combinations which need to be considered. The techniques can constrain the computational complexity of this approach so the number of calculations rises approximately linearly with the number of components present in the sample.

FIGS. 9 and 10 show how the method and apparatus of the present invention work in practice.

FIGS. 9 and 10 show a very simple example which involves a four component problem involving a peak crossover. The sample is a mixture of methyl, ethyl and propyl parabens and anisole. See FIG. 9. The samples were chromatographed on a 10 cm RP8 MPLC cartridge using a ternary solvent system consisting of water, methanol and THF.

The chromatograms shown in FIG. 10 are unnormalized chromatograms showing that the present invention can cope with a significant variation in eluent strength. It should also be noted that even without normalization the retention time behavior is nearly linear with eluent composition.

Component sets are identified in order of their relative area.

The solid, unbroken line 31 shows the lines corresponding to the first component identified.

The second peak is identified by the single chain dotted line 33. Note that in one of the chromatograms (the second chromatogram from the left in FIG. 10) this peak had excess area. This excess area and its retention time is saved and considered in the set of peaks available for identification with the remaining components.

The next component was identified unambiguously as indicated by the dashed line 35. And, finally, the anisole peak was readily found, as indicated by the triple chain dotted line 37. This perhaps is the most interesting case since peak reversal occurs. The present invention succeeds in using this technique in samples containing approximately a dozen peaks. Typically, the calculations involved required less than thirty minutes once the chromatograms have been run.

The success of this technique is determined almost entirely by the quality of the chromatography and peak integration which can be achieved. Errors and incomplete area assignment occur to the extent that the underlying assumptions are violated.

The advantages offered by this technique include:

1. The ability to achieve a complete peak assignment and determination of an optimized separation with no operator intervention other than the initial instrument setup.

2. The hardware used is commercially available off the shelf for a relatively modest price.

3. For constant eluent strength, the optimal ternary eluent composition can be determined in five injections.

4. The technique automatically determines a set of functions describing retention time behavior of each identified component as a function of eluent composition.

5. This permits eluent order correlation without the time consuming task of chromatographing pure components.

The technique is readily generalized to multi-solvent systems.

While I have illustrated and described the preferred embodiments of my invention, it is to be understood that these are capable of variation and modification, and I therefore do not wish to be limited to the precise details set forth, but desire to avail myself of such changes and alterations as fall within the purview of the following claims.

I claim:

1. A method of identifying peaks corresponding to the same chemical component in a series of liquid chromatograms, said method comprising,
chromatographing a sample using several different eluents of approximately the same eluent strength, said eluents being composed of varying mixtures of two binary eluents;
determining the retention times and areas of all peaks in each chromatogram;
forming combinations of peaks, one peak from each chromatogram, such that the set of all combinations of peaks formed is guaranteed to contain a combination of peaks all corresponding to one chemical component of the chromatogram;
testing each combination of peaks in said set by determining the equation of the straight line best describing peak retention times as a function of eluent compositions and computing the relative standard deviations of the set of said straight line to the retention times of the peaks of said combination;
selecting the peak combination and associated straight line factor having the lowest relative standard deviation of any peak combination of the set as containing peaks all corresponding to the same chemical component;
determining the minimum peak area in the identified peak combinations;
removing said minimum peak area from peaks having the retention times of the identified peak configuration; thereby removing this peak area from the collection of peak retention times and areas not identified in each chromatogram; and
repeating formation of sets of peak combinations, testing, selecting, determining and removing until all areas in one chromatogram are assigned or until the relative standard deviation of the best fit straight line exceeds some pre-set threshold.

2. The invention defined in claim 1 including normalizing all peak areas of each chromatogram such that the sum of the areas of all the peaks in each chromatogram is constant.

3. The invention defined in claim 1 including normalizing the retention times of all the peaks in each chromatogram such that the sum overall peaks of each chromatogram of the product of normalized peak area and peak retention times is constant.

4. The invention defined in claim 1 wherein the equation of the straight line is determined according to the least square criterion.

5. The invention defined in claim 1 wherein the equation of the straight line is determined according to the sum of the difference between the absolute value of the computed fit and the placed data point.

6. The invention defined in claim 1 wherein the chromatographing is done using ternary solvent eluents.

7. The invention defined in claim 1 wherein the chromatograms are made using ternary solvent eluents and at least three chromatograms are made.

8. A method of identifying peaks corresponding to the same chemical component in a series of liquid chromatograms, said method comprising,
chromatographing a sample using several different eluents of approximtely the same eluent strength, said eluents being composed of varying mixtures of three binary elements;
determining the retention times and areas of all peaks in each chromatogram;
forming combinations of peaks, one peak from each chromatogram, such that the set of all combinations of peaks formed is guaranteed to contain a combination of peaks all corresponding to one chemical component of the chromatogram;
testing each combination of peaks in said set by determining the equation of the plane best describing peak retention times as a function of eluent compositions and for computing the relative standard deviations of the set of said straight line to the retention times of the peaks of said combination;
selecting the peak combination and associated straight line factor having the lowest relative standard deviation of any peak combination of the set as containing peaks all corresponding to the same chemical component;
determining the minimum peak area in the identified peak combinations;
removing said minimum peak area from peaks having the retention times of the identified peak configuration; thereby removing this peak area from the collection of peak retention times and areas not identified in each chromatogram; and
repeating formation of sets of peak combinations, testing, selecting, determining and removing until all areas in one chromatogram are assigned or until the relative standard deviation of the best fit plane exceeds some pre-set threshold.

9. A method of identifying peaks corresponding to the same chemical component in a series of liquid chromatograms, said method comprising,
chromatographing a sample using several different eluents of approximtely the same eluent strength, said eluents being composed of varying mixtures of n binary elements;
determining the retention times and areas of all peaks in each chromatogram;
forming combinations of peaks, one peak from each chromatogram, such that the set of all combinations of peaks formed is guaranteed to contain a combination of peaks all corresponding to one chemical component of the chromatogram;
testing each combination of peaks in said set by determining the equation of the $n-1$ dimensional plane best describing peak retention times as a function of eluent compositions and for computing the relative standard deviations of the set of said straight line to the retention times of the peaks of said combination;
selecting the peak combination and associated straight line factor having the lowest relative standard deviation of any peak combination of the set as containing peaks all corresponding to the same chemical component;

determining the minimum peak area in the identified peak combinations;

removing said minimum peak area from peaks having the retention times of the identified peak configuration; thereby removing this peak area from the collection of peak retention times and areas not identified in each chromatogram; and repeating formation of sets of peak combinations, testing, selecting, determining and removing until all areas in one chromatogram are assigned or until the relative standard deviation of the best fit $n-1$ dimensional plane exceeds some pre-set threshold.

* * * * *